United States Patent [19]
Dolch

[11] 4,066,069
[45] Jan. 3, 1978

[54] HEART RATE CHANGE SENSOR

[76] Inventor: Volker Dolch, Salzburger Str. 53, Offenbach, Germany, 6050

[21] Appl. No.: 687,534

[22] Filed: May 18, 1976

[51] Int. Cl.² .............................................. A61B 5/04
[52] U.S. Cl. ................................................. 128/2.06 F
[58] Field of Search ...................... 128/2.06 A, 2.06 F, 128/2.06 G, 2.06 R

[56] References Cited
U.S. PATENT DOCUMENTS

| | | | |
|---|---|---|---|
| 3,524,442 | 8/1970 | Horth | 128/2.06 A |
| 3,654,916 | 4/1972 | Neilson | 128/2.06 A |
| 3,759,248 | 9/1973 | Valiquette | 128/2.06 A |
| 3,779,237 | 12/1973 | Goeltz et al. | 128/2.06 A |
| 3,789,159 | 1/1974 | Feit et al. | 128/2.06 A X |
| 3,824,990 | 7/1974 | Baule | 128/2.06 A X |

*Primary Examiner*—William E. Kamm
*Attorney, Agent, or Firm*—Ellsworth R. Roston

[57] ABSTRACT

A reference heart beat is recirculated for comparison with an actual heart beat. First and second voltages are respectively produced with magnitudes representing the rates of recirculation of the reference heart beat and the actual heart beat. A voltage controlled oscillator produces a signal having a variable frequency dependent upon the differences in the first and second voltages. This signal is used to synchronize the rate of the reference heart beat with the rate of the actual heart beat.

The actual heart beat may be separated into progressive segments. The characteristics of the actual heart beat in the progressive segments are compared with the characteristics of the reference heart beat in corresponding segments. An output indication is provided when the characteristics of the actual and reference heart beats in the progressive segments do not coincide. An output indication is also produced when the amplitude of the signals representing the differences between the rates of the actual and reference heart beats experiences abrupt changes.

24 Claims, 7 Drawing Figures

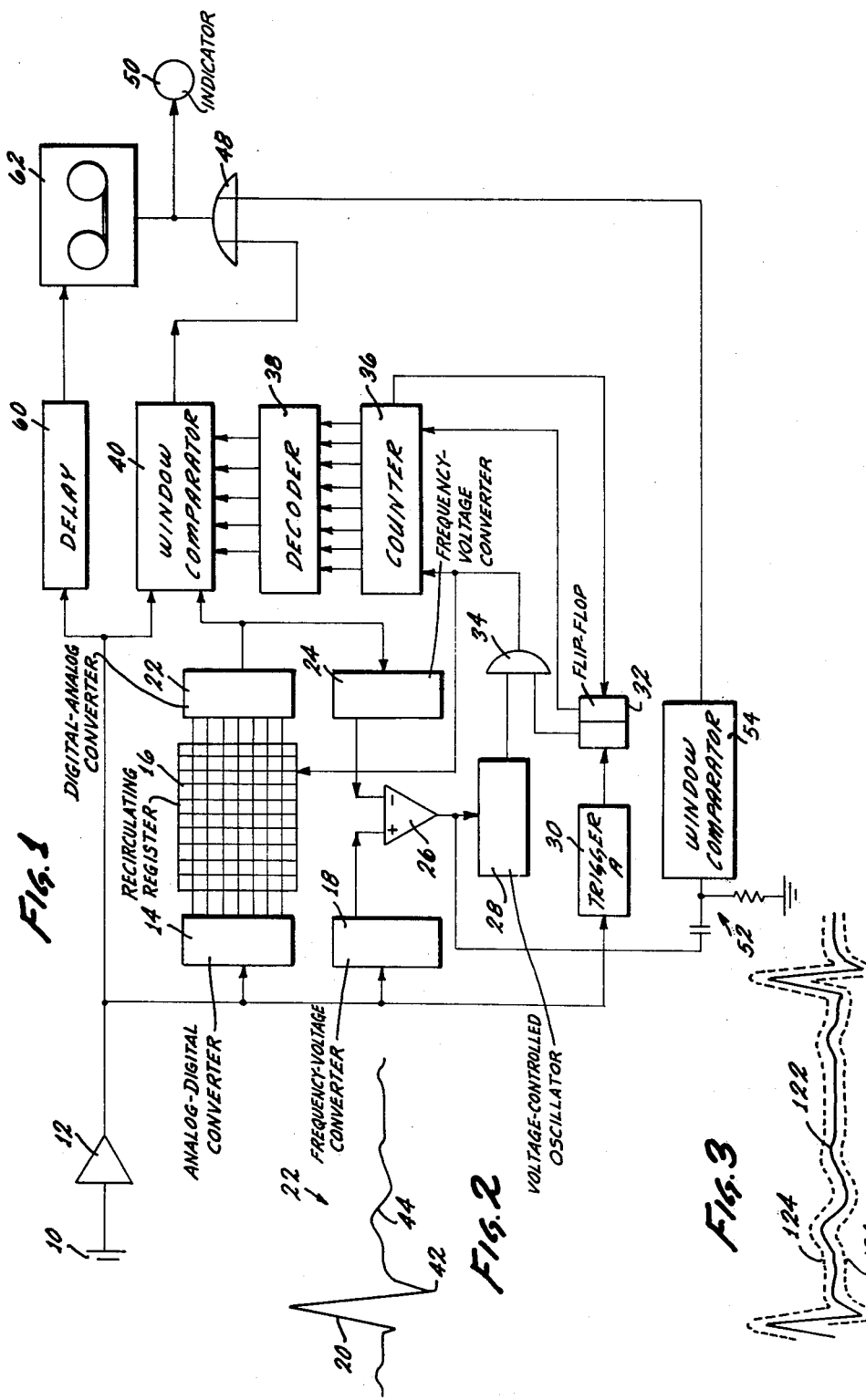

HEART RATE CHANGE SENSOR

This invention relates to a system for testing for the life functions of a patient, such as the heart beat of a patient, to determine if such life functions are proper. More particularly, the invention relates to a system for testing the life functions of a patient in real time and for indicating instantaneously when such life functions are not proper. In this way, the patient is able to take corrective steps promptly to minimize any deleterious effects resulting from such improper life functions.

PRIOR ART

Systems have been developed and are in use for indicating the life functions of a patient to provide a record for future study. For example, systems have been developed and are in use for recording the heart beat of a patient over an extended period of time so that the heart beat can be studied at a subsequent time for irregularity or other possible malfunctions. Although these systems have been helpful in improving the health care of patients, the systems have had certain important limitations. For example, since the systems provide only a record for subsequent study, the systems do not provide an indication on an instantaneous basis of any deficiencies in the life functions at the time that such deficiencies occur. Under such circumstances, the deficiencies or malfunction in the life functions of a patient may continue to the point where the patient becomes seriously injured or dies.

The deficiencies in the systems discussed in the previous paragraph have been recognized for some time. Furthermore, considerable attempts have been made over a long period of time to overcome such deficiencies and provide a system which will operate on an instantaneous basis to evaluate the life functions of a patient and indicate on an instantaneous basis when such life functions become impaired. The efforts over the considerable period of time have been intensive because of the attention devoted over at least the past two or three decades to provide adequate health care to patients. In spite of these intensive efforts, no one has been able to provide a system which operates satisfactorily to indicate on an instantaneous basis the life functions of a patient, such as the heart beat of a patient, and to provide an indication on an instantaneous basis when such life functions become impaired.

FEATURES OF THIS INVENTION

This invention provides a system which overcomes the difficulties set forth above. The system detects the heart beat of a patient and compares this heart beat to a reference heart beat which has been obtained from the patient at a time when the patient's life functions have been operating properly. The system operates on an instantaneous basis to provide an output indication when the actual heart beat of the patient becomes impaired in any way in comparison to the reference heart beat. In this way, the patient is able to take steps promptly to overcome such deficiencies by resting or by taking the proper medicines. The system is relatively light and compact so that it can be easily carried by a patient without any distress or discomfort to the patient.

In one embodiment of the invention, the reference heart beat of a patient is recorded on a suitable member such as a recirculating shift register which recirculates the recorded heart beat at an adjustable frequency. The recorded heart beat is introduced to a frequency-to-voltage converter which operates to produce a voltage in accordance with the rate at which the recorded heart beat is being recirculated in the shift register. The actual heart beats of the patient are introduced to a second converter similar to the first converter. The second converter accordingly operates to produce a voltage in accordance with the rate of occurrence of the actual heart beats.

The voltages from the two converters are introduced to an amplifier which passes to a voltage-controlled oscillator any differences in the voltage between the two converters. The voltage-controlled oscillator produces a signal having a variable frequency dependent upon the difference voltage from the amplifier. The signals from the voltage-controlled oscillator are in turn introduced to the shift register to control the rate of recurrence of the signals from the shift register so that this rate is adjusted over a number of cycles to the rate of the actual heart beat.

The signals representing the actual heart beat are also introduced to a control stage such as a flip-flop which is triggered to a first state such as a set state at a particular instant in each heart beat. When the flip-flop is triggered to the set state, it opens a gate for the passage of the signals from the voltage controlled oscillator to the recirculating register. These signals control the rate of recurrence of the recorded heart beat so that the rate of the recorded heart beat corresponds to the rate of the actual heart beat.

The clock signals from the voltage controlled oscillator are also introduced to a digital counter which counts the signals from the oscillator. When the count in the counter reaches a particular value, a signal passes from the counter to the flip-flop to reset the flip-flop. When the flip-flop becomes reset, signals can no longer be introduced from the voltage controlled oscillator to the recirculating shift register to adjust the rate of recurrence of the recorded heart beat. In this way, means are provided for locking in phase the actual heart beat and the recorded heart beat.

The signals from the counter are introduced to a decoder which operates to decode the count provided by the counter. The activation of the decoder in accordance with the progressive count from the counter causes a comparison to be provided between progressive segments of the actual heart beat and corresponding segments of the recorded heart beat. If the characteristics of the signals representing the progressive segments of the heart beat do not correspond within predetermined limits to the characteristics of the signal representing corresponding segments of the recorded heart beat, an output signal is produced to indicate that the life function of the patient is not proper.

Means may be included in the system for weighting the comparison in different ones of the progressive segments of the actual heart beat so that an output indication is provided in the different segments for individual differences in the characteristics of the actual and recirculating heart beats for such segments. For example, the sensitivity of comparison may be greater in certain selected segments than the sensitivity of comparison in other segments because the characteristics of the heart beat in such selected segments are more important to the life function of the patient than the characteristics of the signal in the other segments and are more important in sustaining full life functions.

Stages are also included in the system constituting this invention for indicating when the rate of the actual heart beat changes abruptly. The production of an output indication for abrupt changes in the rate of the actual heart beat may be important in indicating a fluttering heart beat or in indicating that the heart rate has slowed perceptibly.

Means may also be included in the system for recording on a delayed basis the heart beats preceding an output indication of improper life functions such as heart beats in a patient. The recordal of the heart beats prior to such an output indication may be important in providing a determination subsequently to the patient's doctor of the reasons why such an output indication has been produced. In this way, the doctor may be able to prescribe remedies which will hopefully prevent any recurrences of the improper life functions in the patient.

In the drawings:

FIG. 1 is a drawing, somewhat in block form, showing one embodiment of the system constituting this invention.

FIG. 2 is a curve showing a representative heart beat and further showing a particular triggering point in the heart beat.

FIG. 3 is a curve showing a representative heart beat and also showing the tolerance levels beyond which an output indication is produced.

Figure 4:
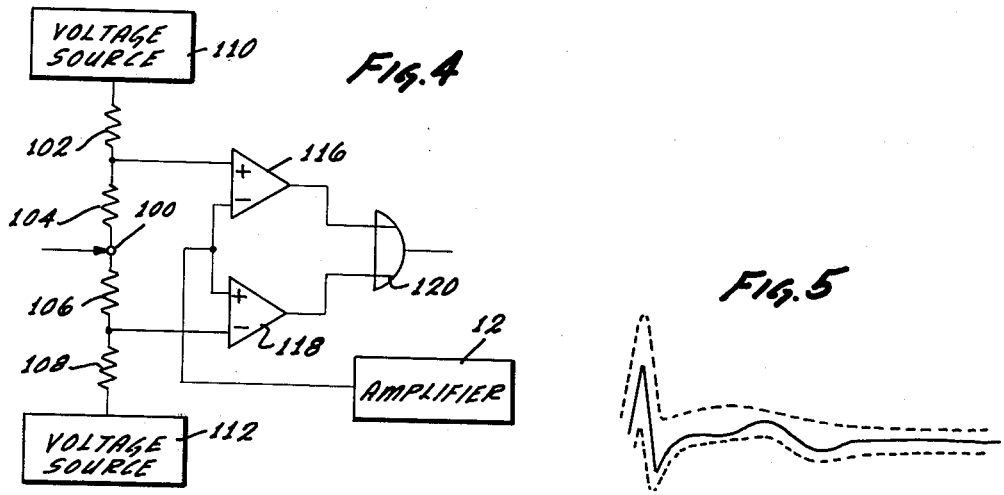
FIG. 4 is a circuit diagram showing in some detail the construction of a comparator which is included in the embodiment shown in FIG. 1.

In the embodiment of the invention shown in FIG. 1, a pickup electrode 10 is adapted to be coupled in a suitable manner to a position on a patient's body near the heart of a patient to receive from the patient signals representing the heart beat of the patient. The signals from the pickup electrode 10 are passed through a preamplifier 12. When a reference signal representing the patient's heart beat is to be recorded in a recirculating shift register 16, the signal is passed through an analog-to-digital converter 14 to the shift register. The converter 14 operates to convert the amplitude of the reference heart beat at each successive instant of time into a corresponding digital representation which is recorded in the shift register 16. The shift register operates to recirculate the digital signals at an adjustable frequency. As will be appreciated, the signal is introduced to the shift register 16 for recirculation at a time when the life functions of the patient are proper. In this way, this recirculating signal can be used for a comparison with the actual heart beats of the patient to indicate when the characteristics of the actual heart beats are not proper.

After the reference signal has been recorded in the shift register 16 for recirculation, the heart beat of the patient passes through the amplifier 12 to a frequency-to-voltage converter 18. The converter 18 is operative to sense the time intervals between successive heart beats of the patient and is particularly operative to sense the time between the production of a particular position in successive heart beats. Such a particular position in each heart beat is illustrated at 20 in a curve illustrated on a general basis at 22 in FIG. 2. The frequency-to-voltage converter 18 may constitute a stage which includes a capacitor that is charged on a linear basis between the point 20 in successive pairs of heart beats such that the stage produces an output voltage having an amplitude corresponding to the time between such successive heart beats. Such a converter is well known in the art.

The output from the recirculating register 16 is also introduced to a digital-to-analog converter 22 which operates to convert the digital representations in the shift register 16 into an analog representation such as that shown in FIG. 2. This representation is in turn introduced to a frequency-to-voltage converter 24 which corresponds to the converter 18 and which is operative to produce a voltage in accordance with the time between the point 20 in successive heart beats recirculating in the register 16.

The voltages from the converters 18 and 24 are introduced to a differential amplifier 26 which provides an output representing the difference between the voltages from the converters. This difference voltage is introduced to a voltage-controlled oscillator 28 which provides signals at a variable frequency dependent upon the voltage from the differential amplifier 26. Such an oscillator is well known in the art.

The signals passing through the amplifier 12 and representing the actual heart beat are also introduced to a trigger circuit 30. The trigger circuit 30 operates to trigger a flip-flop 32 to a particular state such as a set state when the signals representing the heart beat have an amplitude corresponding to the amplitude 20 in FIG. 2. When the flip-flop 22 becomes triggered to the set state, it opens a gate represented by an "AND" network 34 so that the signals from the voltage-controlled oscillator 28 are able to pass through the "AND" gate. These signals are introduced as clock signals to the recirculating shift register 16 to adjust the rate at which the signals recorded in the shift register are recirculated. In this way, the rate of recirculation of the reference signal in the recirculating shift register 16 is adjusted over a number of actual heart beat so that the rate of recirculation of the reference heart beat corresponds to the rate of the actual heart beats.

The signals from the voltage-controlled oscillator also pass through the "AND" network 34 to a digital counter 36. The counter 36 operates to count these clock signals and to provide an output indication of each count. When the count in the counter 36 reaches a particular value, a carry signal is introduced from the counter to the flip-flop 32 to reset the flip-flop.

When the flip-flop 32 becomes reset, the "AND" network 34 becomes closed so that no further signals can pass through the "AND" network from the voltage-controlled oscillator 28 until the flip-flop 32 again becomes triggered to the set stage. Furthermore, when the flip-flop 32 becomes reset, a signal is introduced to the counter 36 from the flip-flop 32 to reset the counter in the counter to a value of "0". By passing the signals from the voltage-controlled oscillator to the counter 36 and triggering the flip-flop 32 to the reset state upon the occurrence of a particular count in the counter and resetting the count in the counter 36, a phase lock loop is produced to insure that the rate of recurrence of the reference signal corresponds precisely to the rate of the actual heart beat.

The signals from the counter 36 are introduced to a decoder 38. The decoder 38 is well known in the art and operates to convert the count in the counter 36 into a form which represents the progressive count and controls the activation in a window comparator 40 of progressive segments of the signals representing the reference and actual heart beats. The comparator 40 operates to control the stringency with which the comparison will be made in the comparator between the characteristics of the signals representing the reference heart beat and the actual heart beat. The comparator 40 provides such a control in accordance with the signals produced in the decoder 38 to represent the progressive segments in the characteristics of the signals representing the heart beats. For example, the portion of the heart beat between positions 42 and 44 in FIG. 2 is often considered to be more critical than other portions of the heart beat. In view of this, a more stringent comparison may be made between the actual and reference heart beats in this portion of the heart beat than in other portions of the heart beat.

The window comparator 40 receives the actual heart beat passing through the amplifier 12 and also receives the reference heart beat recirculating through the converter 22. The window comparator 40 provides a comparison of the characteristics of the actual and reference heart beats at different positions in the heart beats in accordance with the controls provided by the comparator in the progressive portions of the heart beat. When the amplitude characteristics of the actual heart beat differ from the characteristics of the reference heart beat by an amount greater than that specified by the comparator 40, a signal passes from the comparator 40 through an "OR" network 48 to an output indicator 40 which may provide a suitable alarm. This alarm may be aural or visual or a combination of both.

The signals from the amplifier 26 are also introduced to a differentiator which is indicated generally at 52 in FIG. 1 and which may constitute a capacitor and resistor in series between the output from the amplifier and a reference potential such as ground. The differentiator 52 is operative to emphasize relatively rapid changes in the frequency of the signals from the amplifier 26 by increasing the amplitude of the voltage from the amplifier 12 upon the occurrence of such abrupt changes in frequency in comparison to the amplitude of the voltage at other times. The signals passing through the differentiator 52 are compared with signals produced in a window comparator 54 to represent amplitude limits so that only signals representing abrupt changes between the detected and recirculating heart beats are able to pass through the comparator. These signals then pass through the "OR" network 48 to the output indicator 50. In this way, the differentiator 52 and the comparator 54 are operative to sense sudden changes in heart rhythm such as may result from arrhythmia or from heart failure.

As will be appreciated, the indicator 50 provides an indication of improper life functions at the instant that such life functions are not proper. In this way, the patient is able to take remedial steps at the instant that his life functions deteriorate. For example, the patient is able to rest immediately or to take any medicines previously prescribed by his doctor.

It is often desirable to provide a record of the life functions of the patient for a period of time prior to any difficulties in such life functions. A delay line 60 is accordingly provided to delay by a particular time interval the signals passing through the amplifier 12 from the pickup transducer 10. The delayed signals from the line 50 are introduced to a recorder 62 which operates to record the heart beats of the patient for a particular period of time on an updated basis. The operation of the recorder 62 is interrupted by the introduction of a signal passing through the "OR" network 48 so that only the time interval immediately preceding a malfunction in the heart beat of the patient is stored in the recorder. By providing such a record, the patient's doctor is able to study the heart beat of the patient immediately prior to any problems. Such a study may be helpful to the doctor in prescribing any future treatment for the patient.

FIG. 4 illustrates an embodiment of the comparator 40 for controlling the production of output signals by the comparator in accordance with a comparison of the characteristics of the reference heart beat and the actual heart beat. The reference heart beat from the converter 22 is introduced to a terminal 100 in a network formed by a plurality of resistors 102, 104, 106 and 108. The resistors 102, 104, 106 and 108 may have equal values and may be in series. A positive voltage may be introduced from a source 110 to the resistor 102 and a negative voltage of corresponding magnitude may be introduced to the resistor 108 from a source 112.

The voltage on the terminal common to the resistors 102 and 104 is introduced to an amplifier 116 and the voltage on the terminal common to the resistors 106 and 108 is introduced to an amplifier 118. The amplifiers 116 and 118 also receive the signals from the amplifier 12 in representation of the actual heart beat. The signals from the amplifiers 116 and 118 are in turn introduced to an "OR" network 120.

The voltage on the terminal common to the resistors 102 and 104 constitutes an average of the amplitude of the signal representing the reference heart beat at each instant and the positive voltage from the source 110. This voltage and the signals representing the actual heart beat are introduced to the amplifier 116. The amplifier 116 passes a voltage which represents the difference between the amplitude of the signal representing the actual heart beat and the signal introduced to the amplifier from the terminal common to the resistors 102 and 104. This signal ordinarily has a positive amplitude because the voltage on the terminal common to the resistors 102 and 104 is more positive than the amplitude of the signal representing the actual heart beat. In like manner, the amplifier 118 normally passes a signal having a negative amplitude since the amplitude of the signal representing the actual heart beat is more positive than the voltage on the terminal common to the resistors 106 and 108.

Since the window comparator shown in FIG. 4 is symmetrical from an electrical standpoint, the tolerance levels provided by the window comparator shown in FIG. 4 tends to follow the reference voltage. This is shown in FIG. 3. In FIG. 3, the reference heart beat is indicated at 122 and the tolerance levels produced by the signals passing through the amplifiers 116 and 118 are respectively indicated by dotted lines at 124 and 126. As will be seen, the tolerance levels 124 and 126 are symmetrical with respect to the reference heart beat 122 and are equally displaced on opposite sides of the signal representing the reference heart beat. When the amplitude of the signal passing through the amplifier 116 is greater than the difference between the signals 122 and 124 or the amplitude of the signal passing through the amplifier 118 is greater than the differences between the signals 122 and 126, a signal passes through a stage 120. This signal activates the output indicator 50 in FIG. 1.

Figure 6:
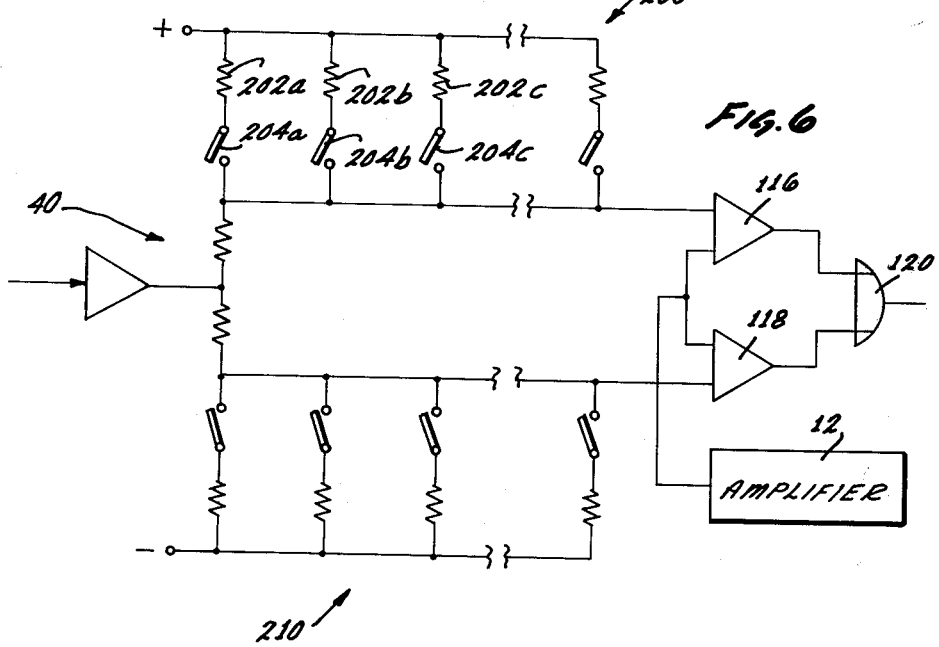
FIG. 6 is a circuit diagram of a comparator which can be used to provide the weighted comparison shown in FIG. 5.

FIG. 6 is a circuit diagram of a comparator which provides a weighted comparison of the signals representing the actual and reference heart beats at progressive segments in these signals. The comparator shown in FIG. 6 includes a first plurality of parallel branches, generally indicated at 200, to replace the resistor 102 in FIG. 4. Each of these branches may include a resistor and a switch in series. For example, a first parallel branch may be formed by a resistor 202a and a switch 204a in series and a second parallel branch may be formed by a resistor 204a and a switch 204b in series. Finally, a second plurality of parallel branches, generally indicated at 210, may be provided to replace the resistor 108 in FIG. 4.

The resistance provided by the branches 200 is dependent upon the combination of switches 202a, 202b, etc., which are closed at each instant. As will be appreciated, the resistance value decreases as the number of switches becomes closed. In this way, by closing different combinations of switches for progressive segments of the actual and reference heart beats, the resistance provided by the branches 200 can be varied. Similarly, different combinations of switches can be closed in the branches 210 to control at each instant the effective value of the resistance provided by these branches. Although a particular construction of the branches 200 and 210 is shown in FIG. 6 and described above, it will be appreciated that the branches can be constructed in other forms without departing from the scope of the invention.

Figure 5:
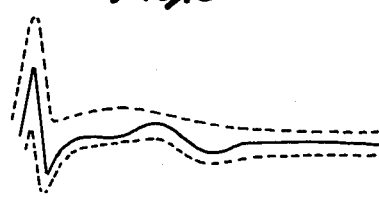
FIG. 5 is a curve similar to that shown in FIG. 3 but illustrating how different portions of the curve can be weighted to change the tolerance levels at individual segments in the curve.
Figure 7:
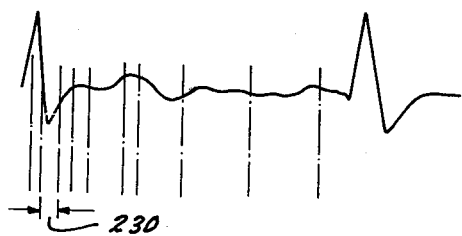
FIG. 7 is a curve of a heart beat similar to that shown in FIGS. 2, 3 and 5 but showing how the heart beat can be divided into individual segments to provide an indication of improper characteristics in the heart beat for the individual segments.

A simple microprocessor may be included in the decoder 38 to control the different combinations of switches which are closed in the branches 200 and 210 for each progressive segment 230 of the signals representing the actual and reference heart beats. One of such segments is shown in FIG. 7. By closing different combinations of switches for each of the progressive segments, a weighting is provided in each of the progressive segments in the comparison between the characteristics of the actual and reference heart beats in such segments. This is indicated in FIG. 5 by the broken lines above and below the reference heart beat 122, which is shown in solid lines. As will be seen, the distance between the solid line and each of the broken lines at any position may be unequal in view of the weighting provided at such positions by the system shown in FIG. 6.

Although this application has been disclosed and illustrated with reference to particular applications, the principals involved are susceptible of numerous other applications which will be apparent to persons skilled in the art. The invention is, therefore, to be limited only as indicated by the scope of the appended claims.

I claim:

1. In combination for detecting changes in the heart beat of a patient,
   first means for prerecording and recirculating a heart beat of the patient,
   second means for detecting each heart beat of the patient and producing signals representing such heart beat,
   third means responsive to the signals from the first and second means for producing signals having characteristics representing any differences between the rates of the heart beats from the first and second means,
   fourth means responsive to the signals from the third means for adjusting the rate of recirculation of the heart beat in the first means in accordance with the characteristics of the signals from the third means,
   fifth means for comparing the characteristics of the recirculated and detected heart beats, and
   sixth means responsive to the signals from the fifth means for providing an indication when the detected heart beat has characteristics different from those of the recirculated heart beat.

2. The combination set forth in claim 1 wherein
   means are included in the fifth means for providing for the introduction of progressive segments of the detected heart beats to the fifth means for comparison with progressive segments of each recirculated heart beat and wherein the sixth means provides an indication when the progressive segments of the detected heart beat have characteristics different from the progressive segments of the recirculated heart beat.

3. The combination set forth in claim 2 wherein
   means are included for weighting the comparison in different ones of the progressive segments of the detected heart beat so that the sixth means is operative to produce an indication in the different segments for individual differences in the characteristics of the detected and recirculated heart beats for such segments.

4. The combination set forth in claim 1 wherein
   the third means include first conversion means for providing a first voltage having a magnitude dependent upon the rate of recirculation of the recorded heart beat and second conversion means for providing a second voltage having a magnitude dependent upon the rate of detection of the heart beats and oscillator means responsive to the first and second voltages for producing a signal having a frequency dependent upon the comparative values of the first and second voltages and wherein the fourth means is responsive to the frequency of the signals from the oscillator means for adjusting the rate of recirculation of the recorded heart beats in accordance with such frequency.

5. In combination for detecting changes in the heart beat of a patient,
   first means for prerecording and recirculating a heart beat of a patient,
   second means for detecting each heart beat of the patient and producing signals representing such heart beat,
   third means responsive to the signals from the first and second means for producing signals having characteristics representing any differences between the rates of the heart beats from the first and second means,
   fourth means responsive to the signals from the third means for producing signals having a variable frequency in accordance with variations in the difference signals from the third means,
   fifth means responsive to the signals from the fourth means for producing an output indication upon abrupt changes in the frequency of the signals from the fourth means, and
   sixth means responsive to the signals from the fourth means for varying the rate of recirculation of the prerecorded heart beat in accordance with the characteristics of the signal from the fourth means.

6. The combination set fourth in claim 5 wherein the third means include first voltage means for providing a first voltage having a magnitude dependent upon the rate of recirculation of the recorded heart beat and second voltage means for providing a second voltage having a magnitude dependent upon the rate of detection of the heart beats and oscillator means responsive to the first and second voltages for producing a signal having a frequency dependent upon the comparative values of the first and second voltages.

7. The combination set forth in claim 6 including means for controlling the passage of signals from the oscillator means to provide a coincidence between rate of recurrence of the the recirculated and detected heart beats.

8. The combination set forth in claim 5 wherein the fifth means includes differentiating means responsive to changes in the magnitudes of the signals from the third means for differentiating such signals to emphasize the signals having frequencies variable at a rate above a particular value and also includes window comparator means for passing from the differentiating means only signals representing abrupt changes in the rate of the detected heart beats.

9. In combination for detecting changes in heart beat of a patient,
   first means for prerecording a heart beat of the patient as a reference
   and for recirculating the prerecorded heart beat at an adjustable frequency to reproduce the prerecorded heart beat on a periodic basis,
   second means for detecting the heart beat of the patient and for producing signals representing the detected heart beat,
   third means responsive to the signals from the first and second means for adjusting the rate of the recirculated heart beat to correspond to the rate of the detected heart beat,
   fourth means for detecting changes in the rate of the recirculated heart beat above a particular value, and
   fifth means responsive to the detected heart beat and the recirculated heart beat for detecting a lack of correspondence between the characteristics of such heart beats.

10. The combination set forth in claim 9, including,
    sixth means responsive to the fourth and fifth means for providing an output indication when at least one of the following occurs (a) the fourth means detects adjustments in the rate of the recirculated heart beat above the particular value or (b) the fifth means detects a lack of correspondence between the characteristics of the detected heart beat and the recirculated heart beat.

11. The combination set forth in claim 10 wherein means are provided for separating each of the detected heart beats into progressive time portions and the sixth means detects a lack of correspondence in the characteristics of such progressive portions with corresponding portions in the recirculated heart beat.

12. The combination set forth in claim 11 wherein means are included for weighting the comparison between the detected heart beats and the reference heart beats in the progressive portions.

13. In combination for detecting changes in the heart beat of a patient,
    means for providing signals representing a reference heart beat of the patient on a recurrent basis,
    means for providing signals representing the actual heart beat of the patient,
    means for comparing the rates of occurrence of the signals representing the reference heart beat and the actual heart beat to provide an error signal representing any differences in rate,
    means responsive to the error signal for adjusting the recurrent rate of the signals representing the reference heart beat in a direction to minimize such error signal, and
    means responsive to the reference heart beat and the actual heart beat for comparing the characteristics representing the reference heart beat and the actual heart beat to provide an output signal when the characteristics of the signals representing the actual heart beat do not correspond to the characteristics of the signals representing the reference heart beat.

14. The combination set forth in claim 13 wherein the comparing means for the rates of occurrence of the signals representing the reference heart beat and the actual heart beat include first means for providing first signals having characteristics representing the rate of recurrence of the signals representing the reference heart beat and second means for providing second signals having characteristics representing the rate of recurrence of the signals representing the actual heart beat and wherein the adjusting means includes oscillator means responsive to the characteristics of the first and second signals for adjusting the recurrent rate of the signals representing the reference heart beat in accordance with any difference in such characteristics.

15. The combination set forth in claim 13 wherein the comparing means for the rates of occurrence of the signals representing the reference heart beat and the actual heart beat include first means for providing a first voltage having a magnitude representing the rate of recurrence of the signals representing the reference heart beat and second means for providing a second voltage having a magnitude representing the rate of the actual heart heart beat and wherein the adjusting means include a voltage controlled oscillator for providing a signal having a frequency variable in accordance with any difference in the magnitude of the first and second voltages for introducing the signal having the variable frequency to the signal means for the reference heart beat to adjust the recurrent rate of the signals representing the reference heart beat.

16. The combination set forth in claim 15, including, means responsive to the first and second voltages for providing signals representing at each instant the differences between such voltages and means responsive to the difference signals for providing an output indication when the amplitude of such difference signals changes at a rate greater than a particular level.

17. The combination set forth in claim 13, including, means responsive to the error signal for providing an output indication when the error signal has characteristics different from particular limits.

18. The combination set forth in claim 17 wherein means are included for weighting the comparison between the actual and reference heart beats at progressive instants of time in each heart beat.

19. In combination for detecting changes in the heart beat of a patient,
means for providing signals representing a reference heart beat of the patient on a recurrent basis,
means for providing signals representing the actual heart beat of the patient,
means for comparing the rates of recurrence of the signals representing the reference heart beat and the actual heart beat to provide an error signal representing any differences in rate,
means responsive to the error signal for adjusting the recurrent rate of the signals representing the reference heart beat in a direction to minimize such error signals, and
means responsive to the error signal for providing an output signal when the error signal varies at a rate above a particular value.

20. The combination set forth in claim 19 wherein the comparing means include a first frequency-to-voltage converter for providing a first signal having voltage characteristics representing the rate of recurrence of the signals representing the recurrent heart beat and a second frequency-to-voltage converter for providing a second signal having voltage characteristics representing the rate of recurrence of the signals representing the actual heart beat and a voltage-controlled oscillator responsive to the voltage characteristics of the first and second signals for providing the error signals with frequency characteristics representing the difference in the voltage characteristics of the first and second signals and wherein
the adjusting means include means responsive to the frequency characteristics of the error signals for adjusting the recurrent rate of the signals representing the recurrent heart beat to minimize such frequency characteristics.

21. The combination set forth in claim 19 wherein the comparing means include first means for providing a first voltage having a magnitude representing the rate of recurrence of the signals representing the recurrent heart beat and second means for providing a second voltage having a magnitude representing the rate of the actual heart beat and third means for providing an error signal having a voltage corresponding to the difference in the first and second voltages and the adjusting means includes a voltage controlled oscillator responsive to the error signal for producing a signal having a frequency variable in accordance with the magnitude of the error voltage and wherein the output signal means provides an output signal when the error signal has abrupt changes.

22. The combination set forth in claim 21 wherein means are responsive to the reference heart beat and the actual heart beat for providing an output indication when the characteristics of the actual heart beat do not correspond to the characteristics of the reference heart beat.

23. The combination set forth in claim 19, including, means responsive to the actual heart beat for separating the heart beat into progressive segments,
means for comparing the characteristics of the heart beat in the progressive segments with the characteristics of the reference heart beat in the progressive segments, and
means for producing an output signal when there is a particular lack of comparison between the characteristics of the progressive segments of the actual heart beat and the corresponding segments of the reference heart beat.

24. The combination set forth in claim 23 wherein means are included for weighting the comparison in the progressive segments of the actual and reference heart beats.

* * * * *